(12) United States Patent
Hochmitz (10) Patent No.: US 7,735,349 B2
(45) Date of Patent: Jun. 15, 2010

(54) CORRELATION OF ULTRASOUND IMAGES AND GATED POSITION MEASUREMENTS

(75) Inventor: Moshe Hochmitz, Kiryat Ata (IL)

(73) Assignee: Biosense Websters, Inc., Diamond Bar, CA (US)

( * ) Notice: Subject to any disclaimer, the term of this patent is extended or adjusted under 35 U.S.C. 154(b) by 458 days.

(21) Appl. No.: 11/669,620

(22) Filed: Jan. 31, 2007

(65) Prior Publication Data

US 2008/0178654 A1      Jul. 31, 2008

(51) Int. Cl.
G01V 13/00        (2006.01)
(52) U.S. Cl. ..................................................... 73/1.82
(58) Field of Classification Search .................. None
See application file for complete search history.

(56) References Cited

U.S. PATENT DOCUMENTS

| | | | |
|---|---|---|---|
| 6,192,735 | B1 | 2/2001 | Nagal |
| 6,517,484 | B1 | 2/2003 | Wilk et al. |
| 6,585,651 | B2 | 7/2003 | Nolte et al. |
| 2004/0254458 | A1 | 12/2004 | Govari |
| 2006/0241445 | A1 | 10/2006 | Altmann et al. |

FOREIGN PATENT DOCUMENTS

WO    WO 2005/039391 A2    5/2005

OTHER PUBLICATIONS

Huang, QH et al. Development of a Portable 3D Ultrasound Imaging System for Musculoskeletal Tissues, Ultrasonics, IPC Science and Technology Press, Ltd, vol. 43, No. 3, pp. 153-163, 2005.

Mercier, L et al. A Review of Calibration Techniques for Freehand 3-D Ultrasound Systems, Ultrasound in Med. & Biol, vol. 31, No. 4, pp. 449-471, 2005.

Prager, RW et al. Stradx: Real-Time Acquisition and Visualization of Freehand Three-Dimensional Ultrasound, Medical Image Analysis, vol. 3, No. 2, pp. 129-140, 1998.

*Primary Examiner*—Robert R Raevis
(74) *Attorney, Agent, or Firm*—Louis J. Capezzuto (57) ABSTRACT

A calibration apparatus includes a motion assembly, which is arranged to move an imaging probe through a calibration point having known coordinates. The imaging probe includes an ultrasound transducer and a position sensor for acquiring concurrently a first sequence of ultrasound images and a second sequence of position measurements. The apparatus further includes a marking circuit, which is arranged to mark an ultrasound image that is acquired by the ultrasound transducer in the first sequence when the imaging probe is at the calibration point. A processor is arranged to calibrate a time offset between the first and second sequences by associating the marked ultrasound image in the first sequence with a position measurement in the second sequence whose coordinates match the coordinates of the calibration point.

25 Claims, 5 Drawing Sheets

CORRELATION OF ULTRASOUND IMAGES AND GATED POSITION MEASUREMENTS

FIELD OF THE INVENTION

The present invention relates generally to medical imaging systems, and particularly to imaging using ultrasound and position tracking systems.

BACKGROUND OF THE INVENTION

Some medical imaging systems track the position of a probe, such as a catheter, which is fitted with a position sensor and an ultrasonic transducer. The position measurements of the probe, coupled with the images produced by the ultrasonic transducer, are used for imaging and/or modeling of a target organ. An exemplary system of this sort is described in U.S. Patent Application Publication 2006/0241445, whose disclosure is incorporated herein by reference.

Several methods and systems are known in the art for calibrating probes that include ultrasound transducers and position sensors. For example, U.S. Patent Application Publication 2004/0254458, whose disclosure is incorporated herein by reference, describes an apparatus for calibrating a probe comprising an ultrasonic transducer and a position measurement device. The apparatus includes a test fixture comprising an ultrasonic target that is disposed therein at a known position. A processor receives a position signal from the position sensor while the transducer aligned to the ultrasonic target determines the orientation of the probe in the frame of reference of the test fixture. The processor determines the calibrated data of the probe related to the orientation.

Additional methods and systems for calibrating ultrasound and position tracking probes are described, for example, in U.S. Pat. Nos. 6,192,735, 6,517,484 and 6,585,651, whose disclosures is incorporated herein by reference.

SUMMARY OF THE INVENTION

There is therefore provided, in accordance with an embodiment of the present invention, a calibration apparatus, including:

a motion assembly, which is arranged to move an imaging probe through a calibration point having known coordinates, the imaging probe including an ultrasound transducer and a position sensor for acquiring concurrently a first sequence of ultrasound images and a second sequence of position measurements;

a marking circuit, which is arranged to mark an ultrasound image that is acquired by the ultrasound transducer in the first sequence when the imaging probe is at the calibration point; and a processor, which is arranged to calibrate a time offset between the first and second sequences by associating the marked ultrasound image in the first sequence with a position measurement in the second sequence whose coordinates match the coordinates of the calibration point.

In some embodiments, the imaging probe includes an electrode that captures a signal for gating the ultrasound images and the position measurements, the marking circuit is arranged to mark the signal that is captured by the electrode when the imaging probe is at the calibration point, and the processor is arranged to calibrate a time delay between the signal and between the first and second sequences using the marked signal. In an embodiment, the signal includes an electrocardiogram (ECG) signal, and the electrode includes an intra-cardiac ECG-sensing electrode.

In another embodiment, the motion assembly includes a wheel and a movable arm, such that a first end of the arm is connected to the wheel and a second end of the arm is attached to the imaging probe, and the wheel is arranged to rotate so as to move the imaging probe through the calibration point.

In a disclosed embodiment, the marking circuit includes an optical emitter, which is arranged to emit light and an optical sensor, which is arranged to sense the light and generate an electrical signal responsively to the sensed light when aligned with the optical emitter, and the optical emitter and the optical sensor are attached to the motion assembly so as to align with one another and generate the electrical signal when the imaging probe is at the calibration point, in order to mark the ultrasound image responsively to the electrical signal.

In yet another embodiment, the marking circuit includes a modulation circuit, which is arranged to generate an ultrasonic marking signal, which has a frequency that can be sensed by the ultrasound transducer, responsively to the electrical signal and to mark the ultrasound image using the ultrasonic marking signal. In still another embodiment, the modulation circuit includes an induction coil, which is located in a vicinity of the imaging probe and is arranged to induce a Radio Frequency (RF) signal in the ultrasound transducer so as to mark the ultrasound image.

In a disclosed embodiment, the processor is arranged to identify the marked ultrasound image by comparing intensity values of the images in the first sequence to a predetermined threshold.

In some embodiments, the calibration point includes two or more different calibration points having known coordinates, the motion assembly is arranged to move the imaging probe through the two or more calibration points, the marking circuit is arranged to mark the ultrasound images acquired by the ultrasound transducer when the imaging probe is at the two or more calibration points, and the processor is arranged to calibrate the time offset between the first and second sequences by associating the marked ultrasound images with respective position measurements whose coordinates match the coordinates of the respective calibration points. Additionally or alternatively, the motion assembly is arranged to move the imaging probe across the calibration point in at least two instances, and the processor is arranged to measure respective values of the time offset at the at least two instances and to average the measured values.

There is additionally provided, in accordance with an embodiment of the present invention, a method for calibration, including:

operating an imaging probe, which includes a position sensor and an ultrasound transducer, so as to acquire concurrently a first sequence of ultrasound images using the ultrasound transducer and a second sequence of position measurements using the position sensor;

moving the imaging probe through a calibration point having known coordinates;

marking an ultrasound image that is acquired by the ultrasound transducer in the first sequence when the imaging probe is at the calibration point; and calibrating a time offset between the first and second sequences by associating the marked ultrasound image in the first sequence with a position measurement in the second sequence whose coordinates match the coordinates of the calibration point.

There is also provided, in accordance with an embodiment of the present invention, a computer software product for use in a calibration apparatus, which includes a motion assembly that moves an imaging probe, which concurrently acquires a first sequence of ultrasound images using an ultrasound transducer and a second sequence of position measurements using a position sensor, through a calibration point having known coordinates, and further includes a marking circuit, which marks an ultrasound image that is acquired by the ultrasound transducer in the first sequence when the imaging probe is at the calibration point, the product including a computer-readable medium, in which program instructions are stored, which instructions, when read by the computer, cause the computer to calibrate a time offset between the first and second sequences by associating the marked ultrasound image in the first sequence with a position measurement in the second sequence whose coordinates match the coordinates of the calibration point.

The present invention will be more fully understood from the following detailed description of the embodiments thereof, taken together with the drawings in which:

DETAILED DESCRIPTION OF EMBODIMENTS

Overview

Some medical imaging procedures use combined ultrasound imaging and position tracking. In such procedures, an intra-body probe, such as a catheter, performs ultrasound imaging of a target organ using an ultrasound transducer. In parallel, the position of the probe in or around the target organ is determined using a position sensor.

When the probe is moved through multiple positions in or around the target organ, an ultrasound imaging subsystem outputs a sequence of two-dimensional (2-D) ultrasound images, which are generated by the ultrasound transducer. In parallel, a position tracking subsystem outputs a sequence of position measurements, which are generated by the position sensor. The position measurements are then used to determine the location and orientation of each of the 2-D ultrasound images in the three-dimensional (3-D) space of the target organ.

In many practical cases, however, the sequence of ultrasound images and the sequence of position measurements are uncorrelated. Generally, the rate at which ultrasound images are acquired may be different from the rate of position measurements, and the two sequences may have an unknown time offset with respect to one another. In order to perform imaging of the target organ, the ultrasound images and position measurements should be correlated with one another, so as to correctly determine the position (location and orientation) of the probe at the time each ultrasound image was acquired.

Embodiments of the present invention provide methods and systems for correlating the sequences of ultrasound images and position measurements. In some embodiments, the probe is placed in a calibration subsystem, which moves the probe through one or more calibration points, whose coordinates are known a-priori. For example, the calibration subsystem may comprise a rotating wheel connected to a moving arm, wherein the probe is attached to the arm. When the probe reaches one of the calibration points, the calibration subsystem produces a pulse, which is used for marking the ultrasound image acquired at this position.

The calibration subsystem further comprises a calibration processor, which identifies the marked ultrasound images and associates them with corresponding position measurements measured at the calibration points. The calibration processor calculates the time offset between the ultrasound images and the corresponding position measurements. The calculated time offset value is stored and used to correlate between the ultrasound images and the position measurements.

System Description

Figure 1:
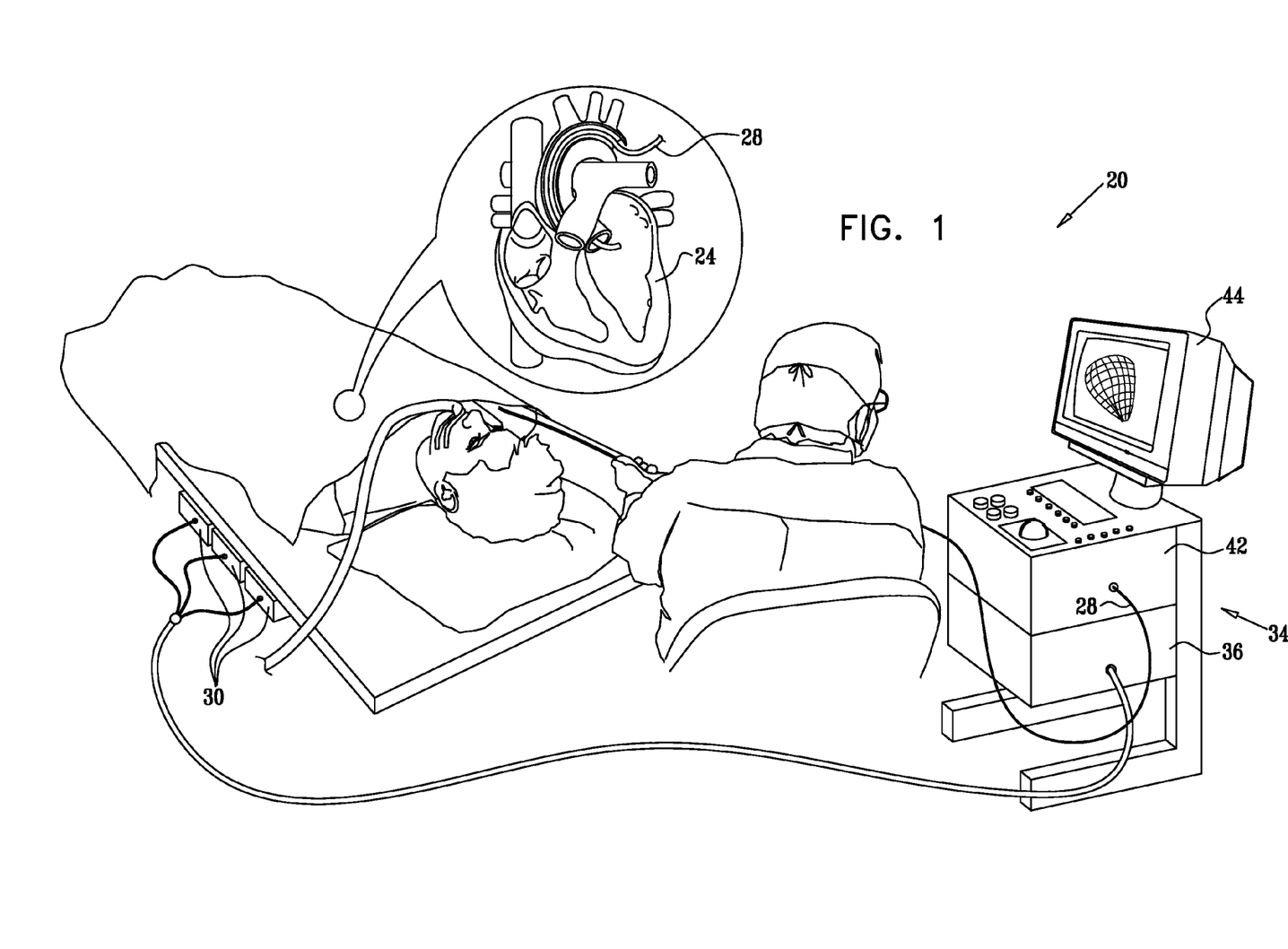
FIG. 1 is a schematic, pictorial illustration of a system for cardiac mapping and imaging, in accordance with an embodiment of the present invention.

FIG. 1 is a schematic, pictorial illustration of a system 20 for imaging and mapping a heart 24 of a patient, in accordance with an embodiment of the present invention. The system comprises a catheter 28, which is inserted by a physician into a chamber of the heart through a vein or artery. The physician can steer, position and orient the distal end of the catheter as desired.

System 20 comprises a position tracking subsystem and an ultrasound imaging subsystem. The position tracking subsystem measures the position (i.e., location and orientation) coordinates of catheter 28. In some embodiments, for example, the position tracking subsystem comprises a magnetic position tracking system. The magnetic position tracking system comprises a set of external radiators, such as field generating coils 30, which are located in fixed, known positions external to the patient. Coils 30 generate magnetic fields in the vicinity of heart 24. A position sensor fitted inside catheter 28 senses the generated magnetic fields and produces position signals in response to the sensed fields. A console 34 comprises a positioning processor 36, which accepts the position signals from catheter 28 and calculates the location and orientation of the catheter based on these signals. In alternative embodiments, the positioning subsystem may comprise any other suitable type of position tracking system, such as impedance-based systems.

The ultrasound imaging subsystem acquires multiple ultrasound images of heart 24. An ultrasound transducer fitted in catheter 28 acquires the ultrasound images, typically comprising 2-D sector-shaped images. Console 34 comprises an image processor 42, which accepts the 2-D ultrasound images and uses them to image heart 24. The output of processor 42 is displayed on a display 44.

Image processor 42 may image heart 24 in a variety of ways. For example, the image processor may use the multiple 2-D images to construct a three-dimensional (3-D) model of the heart. The image processor may also project the acquired 2-D images in 3-D space and present the projected images to a user. Additionally or alternatively, the image processor may register the 2-D ultrasound images with a 3-D image of a different modality, such as a Computerized Tomography (CT) or Magnetic Resonance Imaging (MRI) image, and present the overlaid images to the user. Some aspects of 3-D imaging based on 2-D ultrasound images are described, for example, in U.S. Patent Application Publication 2006/0241445, cited above. Further additionally or alternatively, the image processor may perform any other suitable imaging and/or mapping procedure of heart 24 based on the acquired 2-D ultrasound images.

Figure 2:
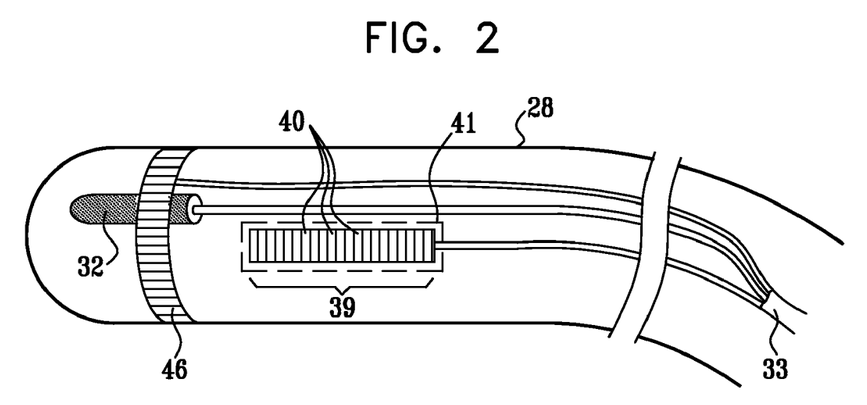
FIG. 2 is a schematic, pictorial illustration of a catheter, in accordance with an embodiment of the present invention.

FIG. 2 is a schematic, pictorial illustration showing the distal end of catheter 28, in accordance with an embodiment of the present invention. Catheter 28 comprises a position sensor 32, and an ultrasound transducer 39, which comprises an array of sensor elements 40. In one embodiment, elements 40 comprise piezo-electric devices. Transducer 39 is positioned in or adjacent to a window 41, which defines an opening within the body or wall of the catheter.

Elements 40 of transducer 39 operate as a phased array, jointly transmitting an ultrasound beam from the array aperture through window 41. In some embodiments, the array transmits a short burst of ultrasound energy and then switches to a receiving mode for receiving the ultrasound signals, or echoes, reflected from the surrounding tissue. After receiving the reflected ultrasound echoes, electric signals based on the reflected echoes are sent by elements 40 over cables 33 through catheter 28 to image processor 42 in console 34, which transforms them into 2-D ultrasound images.

Since some features of the heart change their shape and position during the heart's periodic contraction and relaxation, the imaging methods carried out by image processor 42 are often performed at a particular timing with respect to this period. This process is commonly referred to as gating. In order to perform gated imaging, both the ultrasound images and the position measurements are typically synchronized to an electrocardiogram (ECG) signal. The ECG signal, also referred to as a gating signal, may be produced by a body-surface or intra-cardiac electrode, such as an electrode 46 fitted in catheter 28. In some embodiments, electrode 46 may also be used for performing intra-cardiac ablation for treatment purposes.

As noted above, image processor 42 may perform 3-D imaging of the heart using the 2-D ultrasound images. As part of performing this task, processor 42 positions the 2-D ultrasound images at their appropriate locations and orientations in 3-D space. In order to properly position the ultrasound images, each 2-D ultrasound image should be associated with the position measurement produced by the catheter at the exact time the image was acquired. Inaccurate positioning of the 2-D images would introduce errors and distortion into the 3-D imaging process.

In many practical cases, however, the sequence of ultrasound images generated by the ultrasound imaging subsystem and the sequence of position measurements generated by the positioning subsystem are asynchronous and uncorrelated. For example, in some cases the ultrasound imaging subsystem comprises a standalone unit, such as a commercial imager, which is separate from the position tracking subsystem. The rate of position measurements may be different from the rate of ultrasound image acquisition. Furthermore, the ultrasound imaging subsystem and the positioning subsystem generally have different processing delays. Consequently, the sequence of ultrasound images and the sequence of position measurements usually have a relative time offset, which is not known a-priori.

The methods and systems described herein correlate the ultrasound images with the corresponding position measurements, so that each ultrasound image is associated with the position measurement taken at the time the image was acquired. In some embodiments, such as when the image sequence and the position measurement sequence have a constant relative time offset, this time offset is calculated and used for correlating images and position measurements.

In some embodiments, catheter 28 comprises an ECG-sensing electrode such as electrode 46. The intra-cardiac ECG signal, which is produced by the heart tissue and sensed by electrode 46, may also have a certain time offset with respect to the ultrasound images and/or the position measurements. In these embodiments, a marking signal is also inserted into the gating signal produced by the ECG sensing electrode. The methods and systems described herein can also measure and calibrate the time offset between the ECG signal and between the ultrasound images and position measurements, so that ECG gating can be performed accurately, i.e., at the desired phase of the cardiac cycle.

Figure 3:
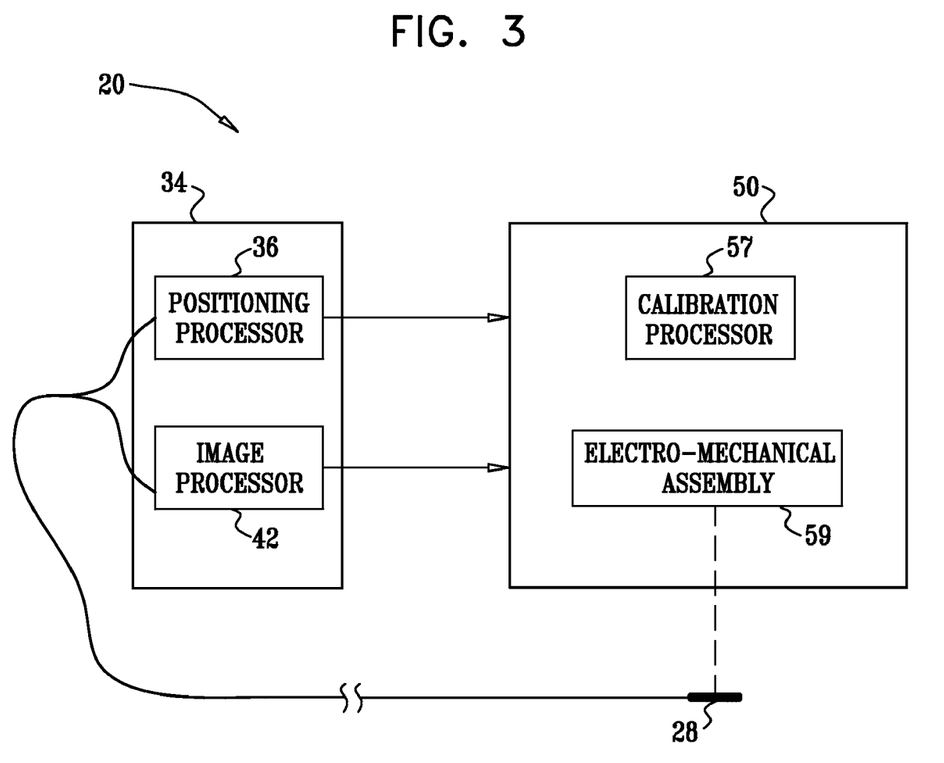
FIG. 3 is a block diagram that schematically illustrates elements of a system for cardiac mapping and imaging, in accordance with an embodiment of the present invention.

FIG. 3 is a block diagram that schematically illustrates elements of system 20, in accordance with an embodiment of the present invention. System 20 comprises a calibration subsystem 50, which comprises an electro-mechanical calibration assembly 59 (also referred to as a motion assembly) and a calibration processor 57. When performing calibration, catheter 28 is placed in the electromechanical assembly. Assembly 59 moves the catheter through one or more calibration points having known a-priori position coordinates. When the calibration subsystem senses that the catheter passes through one of the calibration points, it inserts a distinctive mark into the ultrasound image that is currently acquired by the catheter. When catheter 28 comprises an ECG-sensing electrode, a mark can also be inserted onto the ECG signal produced by this electrode.

Calibration processor 57 accepts the sequence of position measurements from positioning processor 36 and the sequence of 2-D ultrasound images from image processor 42. Processor 57 may also accept the ECG signals produced by electrode 46. The calibration processor associates the marked ultrasound image with the position measurement having the position coordinates of the calibration point in which the image was acquired. Thus, the calibration processor can calculate the time offset between the sequence of ultrasound images and the sequence of position measurements, and to correlate the two sequences. When an ECG signal is also provided, the calibration processor can calculate the time offset between this signal and either the position measurements or the ultrasound images. Generally, the accuracy of the time offset calculation improves with the rate of position measurements and with the rate of the ultrasound images.

Typically, calibration processor 57 is implemented using a general-purpose computer, which is programmed in software to carry out the functions described herein. The software may be downloaded to the computer in electronic form, over a network, for example, or it may alternatively be supplied to the computer on tangible media, such as CD-ROM. In some embodiments, the functionality of calibration processor 57 may be carried out by image processor 42, by another processor in the ultrasound imaging subsystem, by positioning processor 36 or by another processor in the positioning subsystem.

Calibration subsystem 50 may be integrated as part of system 20 and carry out the calibration procedure when the system is initialized. Alternatively, the calibration subsystem may be a separate subsystem, which is connected to system 20 only when calibration is needed. The output of subsystem 50, i.e., the calculated relative time offset value, may be stored in memory and/or provided to image processor 42 or to positioning processor 36 using any suitable interface. Typically, subsystem 50, or at least assembly 59, is located in the working volume of the position tracking subsystem, in order to measure the position coordinates of catheter 28 during calibration.

Figure 4:
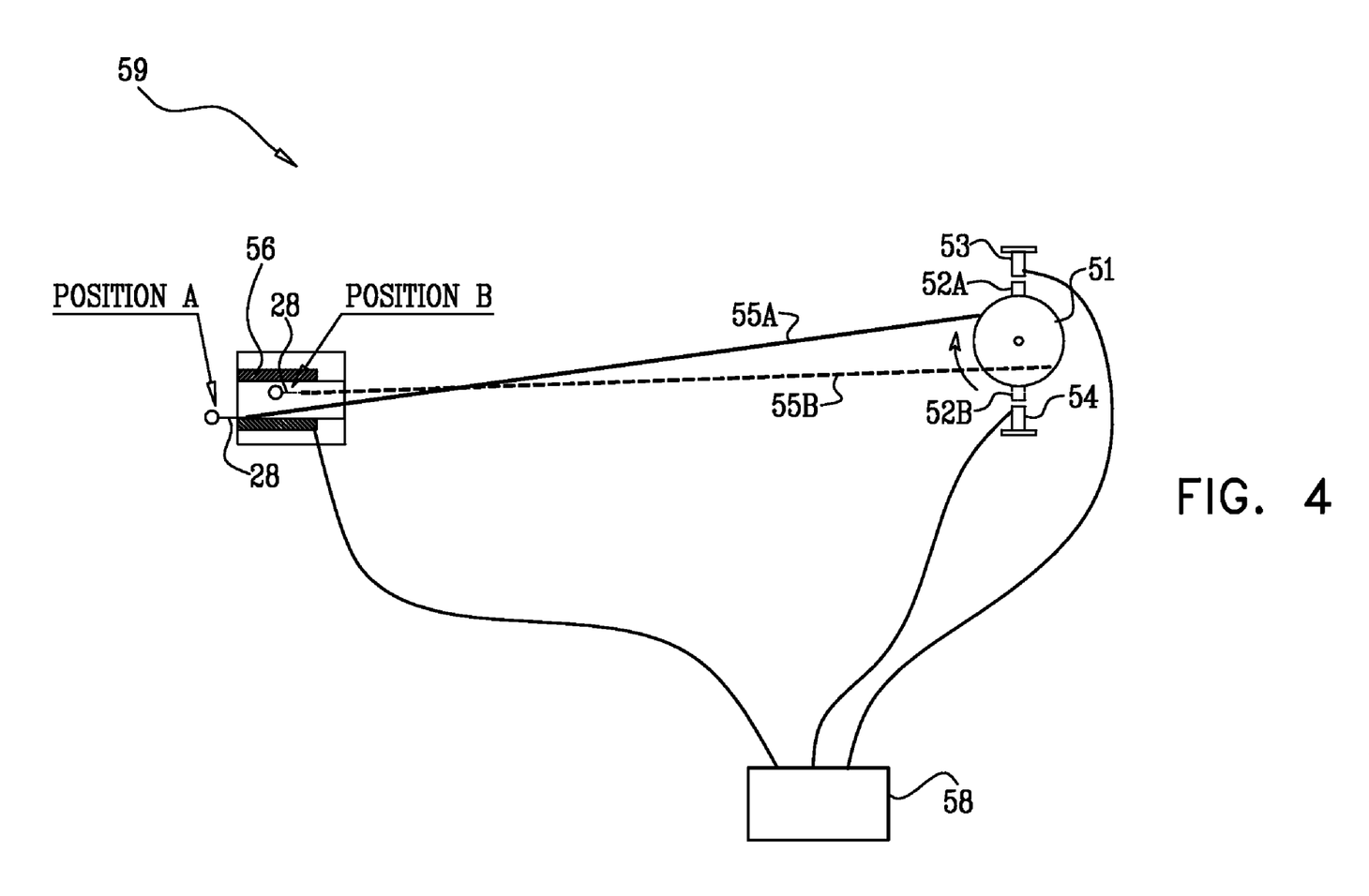
FIG. 4 is a schematic, pictorial illustration of a electromechanical calibration assembly, in accordance with an embodiment of the present invention.

FIG. 4 is a schematic, pictorial illustration that shows electromechanical assembly 59, in accordance with an exemplary embodiment of the present invention. In the exemplary embodiment of FIG. 4, assembly 59 comprises a movable arm (denoted 55A and 55B when positioned at two different positions, as explained below), which is connected to a rotating wheel 51. Catheter 28 is attached to the distal end of the arm during the calibration procedure.

When wheel 51 rotates, such as using a suitable motor, the arm moves catheter 28 through multiple positions. In particular, the catheter passes through two calibration points, or calibration positions, which are denoted "Position A" and "Position B" in the figure. The position coordinates of the calibration points are pre-measured and known in advance. The movable arm is labeled 55A when the catheter is at calibration point A and labeled 55B (dashed) when the catheter is at calibration point B.

An optical emitter, such as a light-emitting diode (LED), is mounted on the perimeter of wheel 51. The optical emitter is shown at two positions in the figure: when the catheter is at calibration point A the emitter is labeled 52A, and when the catheter is at calibration point B the emitter is labeled 52B (dashed). The optical emitter typically emits a narrow light beam outwards from the wheel.

Optical sensors 53 and 54 are mounted adjacently to the external circumference of the rotating wheel, such that when the catheter reaches calibration point A, the emitter is at position 52A and is aligned with optical sensor 53. Similarly, when the catheter reaches calibration point B, the emitter is at position 52B and is aligned with optical sensor 54. Each of the optical sensors generates a short electrical pulse when illuminated by the optical emitter. Thus, sensor 53 generates a pulse when catheter 28 is at calibration point A, and sensor 54 generates a pulse when the catheter is at calibration point B. In some embodiments, sensor 53 emits a positive pulse and sensor 54 emits a negative pulse.

The pulses generated by optical sensors 53 and 54 are provided to a Radio Frequency (RF) modulator 58. Modulator 58 modulates the pulses generated by the emitters onto an RF carrier, whose frequency is in the range used by the ultrasound imaging subsystem. The RF pulses generated by modulator 58 are used to drive an induction coil 56, which is positioned in the vicinity of catheter 28. When triggered, coil 56 induces an RF pulse that is sensed by ultrasound transducer 39 of catheter 28. As a result, the video signal of the ultrasound image that is currently acquired by catheter 28 is marked with a distinct calibration mark. The magnitude of the induced RF pulse is typically chosen so that the intensity of the mark is significantly stronger than any ultrasound echo that might be sensed by transducer 39.

In some embodiments, when using gated imaging, the modulator outputs an additional signal, which is used for marking the gating signal produced by electrode 46, responsively to the pulses generated by optical sensors 53 and 54. The marked gating signal is subsequently used by the calibration processor to calibrate the time offset between the ECG signal and the ultrasound images and/or position measurements.

The modulator and induction coil can be viewed collectively as a modulation circuit, which generates ultrasonic marking signals (e.g., RF pulses) based on the outputs of the optical sensors, and marks the ultrasound images using these marking signals. Alternatively to using an induction coil, the modulation circuit may comprise any other suitable mechanism, which produces an ultrasonic marking signal that can be sensed by ultrasound transducer 39. Further alternatively, the currently-acquired image can be marked by electrically adding a voltage pulse to the signals produced by transducer 39. In alternative embodiments, the optical emitter can be driven with an RF signal, such that the pulses generated by optical sensors 53 and 54 are already modulated, thus eliminating the need for modulator 58.

Typically, the pulse width of the pulses generated by the optical emitters is selected to be sufficiently narrow, so that only a single ultrasound image is marked. Typically, the pulse width is several milliseconds long, significantly shorter than the acquisition time of a single ultrasound image.

As noted above, calibration processor 57 accepts the sequence of ultrasound images and the sequence of position measurements, which are generally uncorrelated. The calibration processor identifies the ultrasound image in which the calibration mark was embedded, such as by comparing the intensity values in the images to a predetermined threshold.

The calibration processor also locates, within the sequence of position measurements produced by the positioning subsystem, a position measurement whose coordinates match (e.g., coincide with or are nearest to) the coordinates of the corresponding calibration point. The time difference between the marked ultrasound image and between the position measurement measured at the corresponding calibration point is indicative of the time offset between the sequence of ultrasound images and the sequence of position measurements.

In some embodiments, the calibration processor calculates the time offset for each of calibration points A and B and averages the result. Alternatively, only a single calibration point may be used. Regardless of the number of calibration points used, the calibration processor may improve the estimation accuracy by rotating wheel 51 several complete rotations and using the generated pulses for averaging a multiplicity of time offset calculations. The calibration processor typically stores the estimated time offset for use during operation of system 20.

Although the exemplary embodiment of FIG. 4 refers to a mechanical assembly that uses an arm and a rotating wheel, the methods and systems described herein can be used with any other suitable motion assembly that moves catheter 28 via the calibration points.

The optical emitter, optical sensors, modulator and induction coil can be viewed collectively as an marking circuit, which marks the currently-acquired ultrasound image when the catheter is in one of the calibration points. Alternatively, any other suitable method, assembly or circuit for producing a trigger signal when the catheter reaches a calibration point and for marking the currently-acquired ultrasound image based on such a trigger, can also be used. For example, the trigger can be produced using a magnet and a magnetic sensor, a laser source and an optical sensor, a volume sensor, or any other suitable mechanism.

Figure 5:
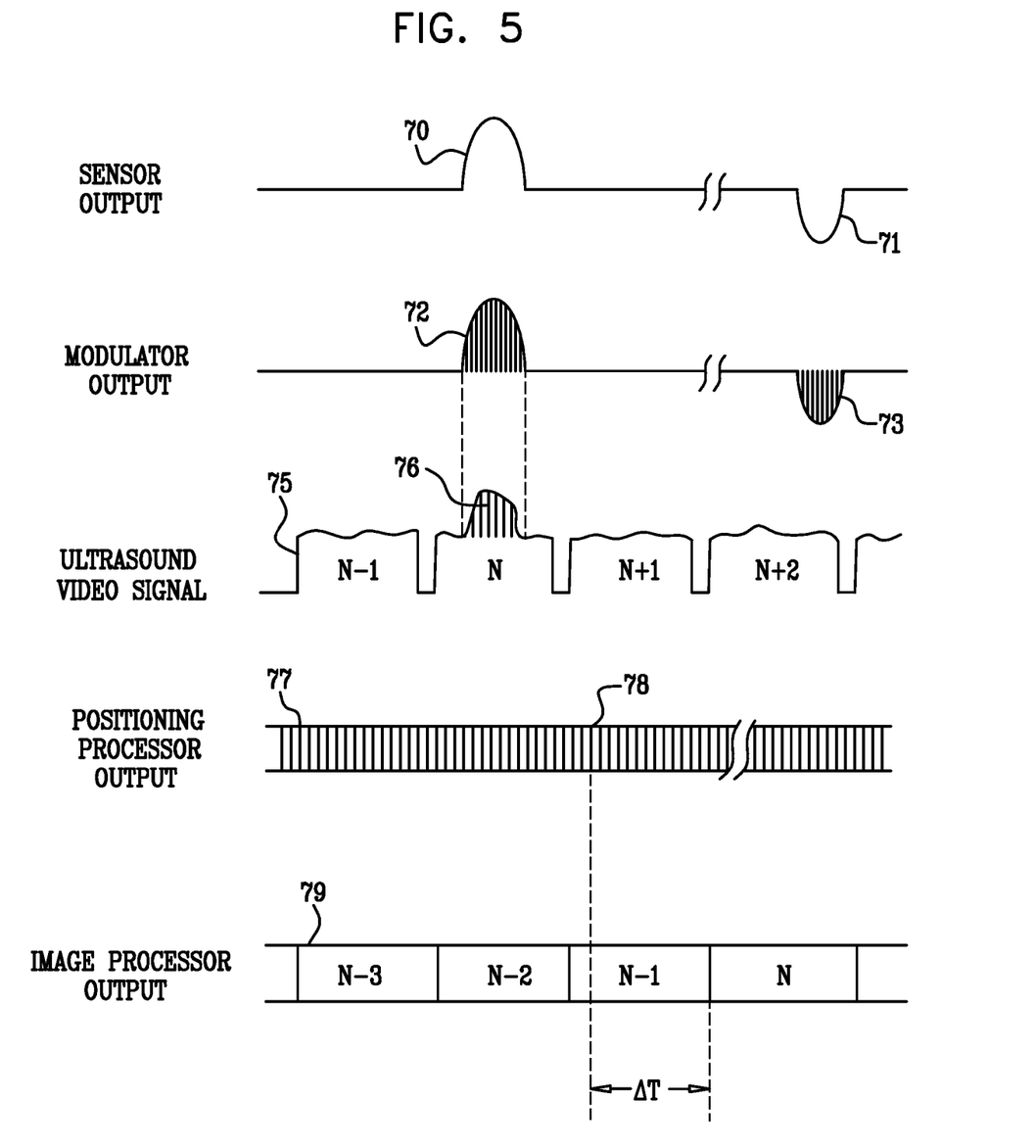
FIG. 5 is a signal timing diagram showing correlation of position measurements with ultrasound images, in accordance with an embodiment of the present invention.

FIG. 5 is a signal timing diagram showing an exemplary process of correlating position measurements with ultrasound images, in accordance with an embodiment of the present invention. Electrical pulses 70 and 71 are generated by optical emitters 53 and 54 when catheter 28 reaches calibration points A and B, respectively. Pulses 72 and 73 denote the modulated RF pulses produced by modulator 58 in response to pulses 70 and 71, respectively. A plot 75 shows the video signal of the ultrasound images acquired by transducer 39 of catheter 28. Successive ultrasound images are denoted N−1, N, N+1, . . . The video signal of image N is marked with a calibration mark 76 responsively to pulse 72. The mark that corresponds to pulse 73 is not shown for the sake of clarity.

A measurement sequence 77 denotes the sequence of position measurements produced by positioning processor 36. A position measurement 78 denotes the position measurement whose coordinates match the coordinates of calibration point A. A measurement sequence 79 denotes the sequence of ultrasound images produced by image processor 42. As can be appreciated, the delay between the image acquisition by catheter 28 (plot 75) and between the output of the image processor (sequence 79) may be several image cycles long.

As explained above, calibration processor 57 estimates the time offset between the marked image (image N) in sequence 79 and between the position measurement measured at calibration point A (measurement 78). This time offset is denoted ΔT in the figure. Although in the present example the offset is measured with respect to the beginning of the marked image, the offset can alternatively be measured with respect to the end of the marked image or to any other suitable reference point in the image.

Calibration Method Description

Figure 6:
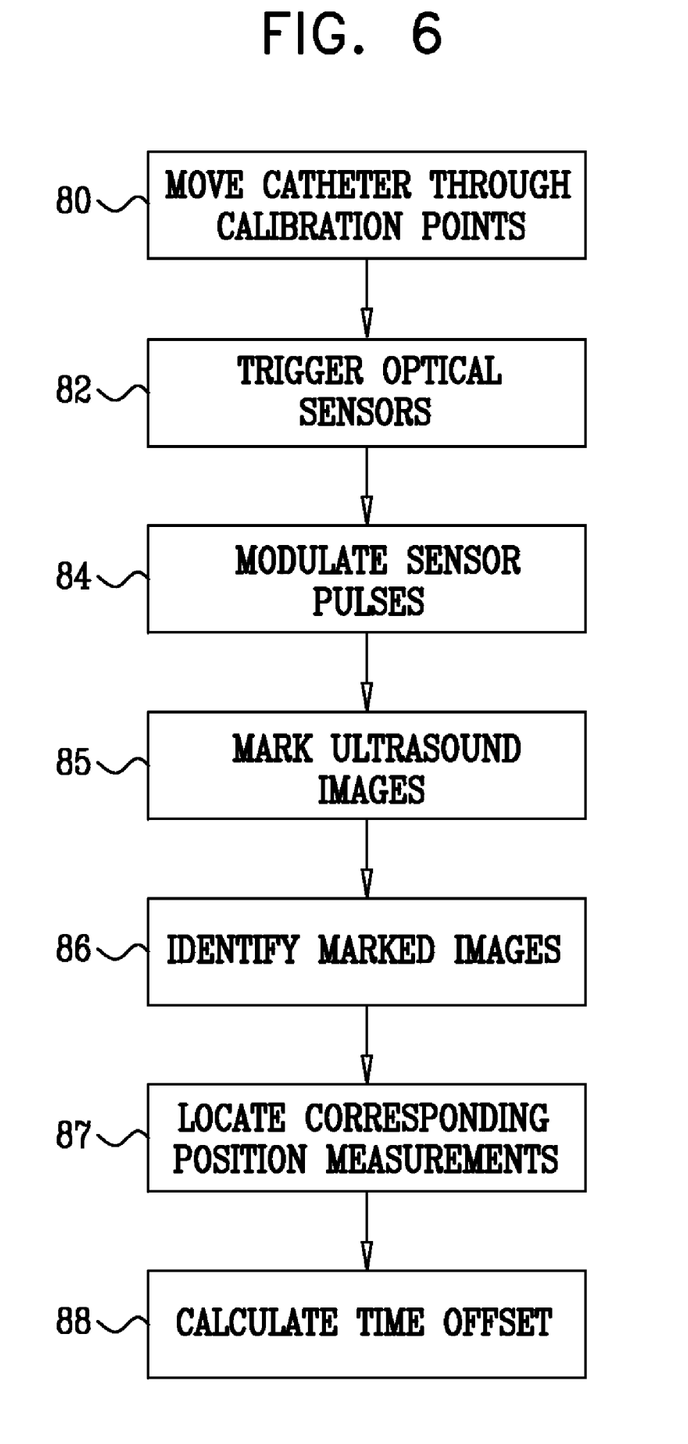
FIG. 6 is a flow chart that schematically illustrates a method for correlating position measurements with ultrasound images, in accordance with an embodiment of the present invention.

FIG. 6 is a flow chart that schematically illustrates a method for correlating position measurements with ultrasound images, in accordance with an embodiment of the present invention. The method begins with assembly 59 moving catheter 28 through the different calibration points, at a catheter scanning step 80.

When the catheter reaches one of the calibration points, the optical emitter aligns with one of optical sensors 53 and 54. As a result, the optical sensor aligned with the emitter produces a pulse, at a pulse generation step 82. Modulator 58 modulates the pulse generated by the optical sensor, at a modulation step 84. Induction coil 56 marks the video signal of the currently-acquired ultrasound image, at an image marking step 85. The process of steps 80-85 above can be repeated for one or more calibration points and/or for multiple measurements of each calibration point.

Calibration processor 57 identifies the marked images in the sequence of ultrasound images produced by image processor 42, at an image identification step 86. For each identified marked image, the calibration processor locates the position measurement, whose coordinates match the coordinates of the calibration point in question, at a position measurement identification step 87. The calibration processor calculates the time offset between each marked image and the corresponding position measurement, at a time offset calculation step 88. The calibration processor typically averages the different measured time offsets in order to improve the estimation accuracy. The calculated and averaged time offset is stored and subsequently used for coordinating between the ultrasound images and position measurements during operation of system 20.

Although the embodiments described herein mainly address calibration of a catheter-based imaging system, the principles of the present invention can also be used for calibrating other types of probes fitted with position sensors and ultrasound transducers, such as endoscopes. Although the embodiments described herein mainly refer to imaging of the heart, the principles of the present invention can also be used for imaging and modeling of other organs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A calibration apparatus, comprising:
a motion assembly, which is arranged to move an imaging probe through a calibration point having known coordinates, the imaging probe including an ultrasound transducer and a position sensor for acquiring concurrently a first sequence of ultrasound images and a second sequence of position measurements;
a marking circuit, which is arranged to mark an ultrasound image that is acquired by the ultrasound transducer in the first sequence when the imaging probe is at the calibration point; and
a processor, which is arranged to calibrate a time offset between the first and second sequences by associating the marked ultrasound image in the first sequence with a position measurement in the second sequence whose coordinates match the coordinates of the calibration point.

2. The apparatus according to claim 1, wherein the motion assembly comprises a wheel and a movable arm, wherein a first end of the arm is connected to the wheel and a second end of the arm is attached to the imaging probe, and wherein the wheel is arranged to rotate so as to move the imaging probe through the calibration point.

3. The apparatus according to claim 1, wherein the marking circuit comprises an optical emitter, which is arranged to emit light and an optical sensor, which is arranged to sense the light and generate an electrical signal responsively to the sensed light when aligned with the optical emitter, and wherein the optical emitter and the optical sensor are attached to the motion assembly so as to align with one another and generate the electrical signal when the imaging probe is at the calibration point, in order to mark the ultrasound image responsively to the electrical signal.

4. The apparatus according to claim 3, wherein the marking circuit comprises a modulation circuit, which is arranged to generate an ultrasonic marking signal, which has a frequency that can be sensed by the ultrasound transducer, responsively to the electrical signal and to mark the ultrasound image using the ultrasonic marking signal.

5. The apparatus according to claim 4, wherein the modulation circuit comprises an induction coil, which is located in a vicinity of the imaging probe and is arranged to induce a Radio Frequency (RF) signal in the ultrasound transducer so as to mark the ultrasound image.

6. The apparatus according to claim 1, wherein the processor is arranged to identify the marked ultrasound image by comparing intensity values of the images in the first sequence to a predetermined threshold.

7. The apparatus according to claim 1, wherein the motion assembly is arranged to move the imaging probe through two or more calibration points having known coordinates, wherein the marking circuit is arranged to mark the ultrasound images acquired by the ultrasound transducer when the imaging probe is at the two or more calibration points, and wherein the processor is arranged to calibrate the time offset between the first and second sequences by associating the marked ultrasound images with respective position measurements whose coordinates match the coordinates of the respective calibration points.

8. The apparatus according to claim 1, wherein the motion assembly is arranged to move the imaging probe across the calibration point in at least two instances, and wherein the processor is arranged to measure respective values of the time offset at the at least two instances and to average the measured values.

9. The apparatus according to claim 1, wherein the imaging probe includes an electrode that produces a gating signal for gating the ultrasound images and the position measurements, wherein the marking circuit is arranged to mark the gating signal that is produced by the electrode when the imaging probe is at the calibration point, and wherein the processor is arranged to calibrate a time delay between the gating signal and between the first and second sequences using the marked gating signal.

10. The apparatus according to claim 9, wherein the gating signal comprises an electrocardiogram (ECG) signal, and wherein the electrode comprises an intra-cardiac ECG-sensing electrode.

11. A method for calibration, comprising:
operating an imaging probe, which includes a position sensor and an ultrasound transducer, so as to acquire concurrently a first sequence of ultrasound images using the ultrasound transducer and a second sequence of position measurements using the position sensor;
moving the imaging probe through a calibration point having known coordinates;
marking an ultrasound image that is acquired by the ultrasound transducer in the first sequence when the imaging probe is at the calibration point; and
calibrating a time offset between the first and second sequences by associating the marked ultrasound image in the first sequence with a position measurement in the second sequence whose coordinates match the coordinates of the calibration point.

12. The method according to claim 11, and comprising inserting the imaging probe into an organ of a patient and imaging the organ by associating at least some of the ultrasound images in the first sequence with respective position measurements in the second sequence.

13. The method according to claim 11, wherein moving the imaging probe comprises attaching the imaging probe to a first end of a movable arm whose second end is connected to a wheel, and rotating the wheel so as to move the imaging probe though the calibration point.

14. The method according to claim 11, wherein marking the ultrasound image comprises positioning an optical emitter, which emits light and an optical sensor, which senses the light and generates an electrical signal responsively to the sensed light when aligned with the optical emitter, to align with one another and generate the electrical signal when the imaging probe is at the calibration point, and marking the ultrasound image responsively to the electrical signal.

15. The method according to claim 14, wherein marking the ultrasound image comprises generating an ultrasonic marking signal, which has a frequency that can be sensed by the ultrasound transducer, responsively to the electrical signal, and marking the ultrasound image using the ultrasonic marking signal.

16. The method according to claim 15, wherein marking the ultrasound image using the ultrasonic marking signal comprises inducing a Radio Frequency (RF) signal in the ultrasound transducer using an induction coil, which is located in a vicinity of the imaging probe.

17. The method according to claim 11, wherein calibrating the time offset comprises identifying the marked ultrasound image by comparing intensity values of the images in the first sequence to a predetermined threshold.

18. The method according to claim 11, wherein moving the imaging probe comprises moving the probe through two or more different calibration points having known coordinates, wherein marking the ultrasound image comprises marking the ultrasound images acquired by the ultrasound transducer when the imaging probe is at the two or more calibration points, and wherein calibrating the time offset between the first and second sequences comprises associating the marked ultrasound images with respective position measurements whose coordinates match the coordinates of the respective calibration points.

19. The method according to claim 11, wherein moving the imaging probe comprises crossing the calibration point in at least two instances, and wherein calibrating the time offset comprises measuring values of the time offset at the at least two instances and averaging the measured values.

20. The method according to claim 11, wherein the imaging probe includes an electrode that produces a gating signal for gating the ultrasound images and the position measurements, and comprising marking the gating signal that is produced by the electrode when the imaging probe is at the calibration point, and calibrating a time delay between the gating signal and between the first and second sequences using the marked gating signal.

21. The method according to claim 20, wherein the gating signal comprises an electrocardiogram (ECG) signal, and wherein the electrode comprises an intra-cardiac ECG-sensing electrode.

22. A computer software product for use in a calibration apparatus, which includes a motion assembly that moves an imaging probe, which concurrently acquires a first sequence of ultrasound images using an ultrasound transducer and a second sequence of position measurements using a position sensor, through a calibration point having known coordinates, and further includes a marking circuit, which marks an ultrasound image that is acquired by the ultrasound transducer in the first sequence when the imaging probe is at the calibration point, the product comprising a computer-readable medium, in which program instructions are stored, which instructions, when read by the computer, cause the computer to calibrate a time offset between the first and second sequences by associating the marked ultrasound image in the first sequence with a position measurement in the second sequence whose coordinates match the coordinates of the calibration point.

23. The product according to claim 22, wherein the instructions cause the computer to identify the marked ultrasound image by comparing intensity values of the images in the first sequence to a predetermined threshold.

24. The product according to claim 22, wherein the calibration point comprises two or more different calibration points having known coordinates, wherein the motion assembly moves the imaging probe through the two or more calibration points, wherein the marking circuit marks the ultrasound images acquired by the ultrasound transducer when the imaging probe is at the two or more calibration points, and wherein the instructions cause the computer to calibrate the time offset between the first and second sequences by associating the marked ultrasound images with respective position measurements whose coordinates match the coordinates of the respective calibration points.

25. The product according to claim 22, wherein the motion assembly moves the imaging probe across the calibration point in at least two instances, and wherein the instructions cause the computer to measure respective values of the time offset at the at least two instances and to average the measured values.

* * * * *

UNITED STATES PATENT AND TRADEMARK OFFICE
CERTIFICATE OF CORRECTION

PATENT NO. : 7,735,349 B2  Page 1 of 1
APPLICATION NO. : 11/669620
DATED : June 15, 2010
INVENTOR(S) : Moshe Hochmitz It is certified that error appears in the above-identified patent and that said Letters Patent is hereby corrected as shown below:

On the Title Page, Item (73) Assignee: Please remove "Biosense Websters, Inc." and replace with Biosense Webster, Inc.

Signed and Sealed this

Third Day of August, 2010

David J. Kappos
*Director of the United States Patent and Trademark Office*